United States Patent
Kirkpatrick et al.

(10) Patent No.: US 6,491,800 B2
(45) Date of Patent: Dec. 10, 2002

(54) METHOD AND SYSTEM FOR IMPROVING THE EFFECTIVENESS OF ARTIFICIAL HIP JOINTS BY THE APPLICATION OF GAS CLUSTER ION BEAM TECHNOLOGY

(75) Inventors: Allen R. Kirkpatrick, Lexington, MA (US); Vincent DiFilippo, Woburn, MA (US)

(73) Assignee: Epion Corporation, Billerica, MA (US)

(*) Notice: Subject to any disclaimer, the term of this patent is extended or adjusted under 35 U.S.C. 154(b) by 0 days.

(21) Appl. No.: 09/901,203

(22) Filed: Jul. 9, 2001

(65) Prior Publication Data

US 2002/0017455 A1 Feb. 14, 2002

Related U.S. Application Data

(60) Provisional application No. 60/217,313, filed on Jul. 10, 2000.

(51) Int. Cl.[7] .................... C23C 14/34; C23C 14/02; B44C 1/22; B05D 3/00
(52) U.S. Cl. .................... 204/192.34; 204/298.36; 204/298.28; 216/66; 216/38; 427/2.24; 427/534
(58) Field of Search .................... 204/298.04, 298.15, 204/298.36, 298.28, 192.11, 192.34; 216/66, 38; 427/2.24, 534; 623/22.11; 118/723 CB

(56) References Cited

U.S. PATENT DOCUMENTS

| 4,968,006 A | 11/1990 | Oliver .................... 266/78 |
| 5,123,924 A | 6/1992 | Sioshansi et al. .............. 623/16 |
| 5,133,757 A | 7/1992 | Sioshansi et al. .............. 623/18 |
| 5,814,194 A | * 9/1998 | Deguchi et al. ......... 204/192.1 |
| 5,980,974 A | 11/1999 | Armini et al. .............. 427/227 |

\* cited by examiner

*Primary Examiner*—Steven H. VerSteeg
(74) *Attorney, Agent, or Firm*—Perkins, Smith & Cohen, LLP; Jerry Cohen

(57) ABSTRACT

The application of gas cluster ion beam (GCIB) technology in order to modify the surface of a surgical implant such as the components of an artificial hip joint, thereby substantially reducing wear debris and osteolysis complications is disclosed. The approach of the surface modification comprises an atomic level surface smoothing utilizing GCIB to super smooth the femoral heads and/or the surfaces of the acetabular cups to reduce frictional wear at the interface of the bearing surfaces. A reduction in polyethylene debris and metal debris by GCIB smoothing on one or both bearing surfaces of a surgical implant reduces osteolysis, results in a substantial cost savings to the healthcare system, and reduces patient pain and suffering.

37 Claims, 5 Drawing Sheets

METHOD AND SYSTEM FOR IMPROVING THE EFFECTIVENESS OF ARTIFICIAL HIP JOINTS BY THE APPLICATION OF GAS CLUSTER ION BEAM TECHNOLOGY

CROSS REFERENCE TO RELATED APPLICATIONS

This application claims priority of U. S. provisional application Ser. No. 60/217,313 entitled "Method and System for Improving the Effectiveness of Artificial Hip Joints by the Application of Gas Cluster Ion Beam Technology", filed Jul. 10, 2000, the provisional application being incorporated herein by reference.

FIELD OF THE INVENTION

This invention relates generally to medical devices or surgical implants such as artificial hip joints and, more particularly to a method and system for smoothing surgical implants such as artificial hip joints using gas cluster ion beam technology.

BACKGROUND OF THE INVENTION

Total hip replacement, or arthroplasty, is a surgical procedure in which the diseased parts of a hip joint are removed and replaced with new, artificial parts. Presently, these artificial hip joint components are being produced from improved bearing materials such as highly cross-linked polyethylene, metal-on-metal, and ceramic-on-ceramic implants. After the hip replacement, osteolysis is a major problem and is believed to be due to an inflammatory process brought on by particulate matter or debris dislodged from the implants themselves. Some degree of osteolysis is present in up to 40% of all cases within 10 years of surgery.

The problem is articulating surfaces between the femoral and acetabular components of the implant produce wear debris which is an important contributor to pathologic tissue response. Therefore, the long-term threat to component failure from a biologic standpoint is this wearing debris associated with osteolysis. The critical initiating sequence involves the interaction between small particulate materials and responding specialized cells. The number, size, distribution, and type of particulate material are also believed to have an affect on the process.

Quantitatively, the material causing the most tissue reaction appears to be the particulate polyethylene with particle sizes of approximately 0.5 micron. Metallic debris also causes tissue reaction with significant quantities identified with particle sizes somewhat larger than the polyethylene debris. The major effect of this larger metallic debris may relate to promoting wear of the polyethylene, with the derivative polyethylene particles of submicron size triggering the cellular response. However, smaller metal particles and ions have been demonstrated to be active in direct stimulation of biologic processes as well.

It is therefore an object of this invention to provide an atomic level surface smoothing of artificial hip joints.

It is a further object of this invention to provide surface modification of artificial hip joints by gas cluster ion beams to alleviate the problems associated with osteolysis.

SUMMARY OF THE INVENTION

The objects set forth above as well as further and other objects and advantages of the present invention are achieved by the invention described hereinbelow.

Several factors have been suggested to minimize the production of wear debris: (1) femoral heads with highly polished cobalt alloy or polished ceramics are believed to be advantageous in minimizing effects of wear on the polyethylene surfaces of the acetabular cups; (2) new highly cross-linked polyethylene acetabular cups are gaining some increased surgical use as a means of decreasing wear and; (3) hard-on-hard implants such as metal-on-metal and ceramic-on-ceramic implants are expected to reduce wear debris.

Regardless of the materials used in the artificial hip joint designs, the present invention applies gas cluster ion beam (GCIB) technology in order to modify the component's surface, thereby substantially reducing wear debris and osteolysis complications. The approach of the surface modification comprises an atomic level surface smoothing utilizing GCIB to super smooth the femoral heads and/or the surfaces of the acetabular cups to reduce frictional wear at the interface of the bearing surfaces.

A reduction in polyethylene debris and metal debris by GCIB smoothing on one or both bearing surfaces of a total hip prosthesis reduces osteolysis, results in a substantial cost savings to the healthcare system, and reduces patient pain and suffering.

For a better understanding of the present invention, together with other and further objects thereof, reference is made to the accompanying drawings and detailed description and its scope will be pointed out in the appended claims.

DETAILED DESCRIPTION OF THE PREFERRED METHODS AND EMBODIMENTS

Beams of energetic ions, electrically charged atoms or molecules accelerated through high voltages under vacuum, are widely utilized to form semiconductor device junctions, to smooth surfaces by sputtering, and to enhance the properties of thin films. Gas cluster ions are formed from large numbers of weakly bound atoms or molecules sharing common electrical charges and accelerated together through high voltages to have high total energies. Cluster ions disintegrate upon impact and the total energy of the cluster is shared among the constituent atoms. Because of this energy sharing, the atoms are individually much less energetic than the case of conventional ions or ions not clustered together and, as a result, the atoms penetrate to much shorter depths. Surface sputtering effects are orders of magnitude stronger than corresponding effects produced by conventional ions, thereby making important microscale surface smoothing effects possible that are not possible in any other way.

The concept of gas cluster ion beam (GCIB) processing has only emerged over the past decade. Using a GCIB for dry etching, cleaning, and smoothing of materials is known in the art and has been described, for example, by Deguchi, et al. in U.S. Pat. No. 5,814,194, "Substrate Surface Treatment Method", 1998. Because ionized clusters containing on the order of thousands of gas atoms or molecules may be formed and accelerated to modest energies on the order of a few thousands of electron volts, individual atoms or molecules in the clusters may each only have an average energy on the order of a few electron volts. It is known from the teachings of Yamada in, for example, U.S. Pat. No. 5,459,326, that such individual atoms are not energetic enough to significantly penetrate a surface to cause the residual subsurface damage typically associated with plasma polishing. Nevertheless, the clusters themselves are sufficiently energetic (some thousands of electron volts) to effectively etch, smooth, or clean hard surfaces.

Because the energies of individual atoms within a gas cluster ion are very small, typically a few eV, the atoms penetrate through only a few atomic layers, at most, of a target surface during impact. This shallow penetration of the impacting atoms means all of the energy carried by the entire cluster ion is consequently dissipated in an extremely small volume in the top surface layer during a period on the order of $10^{-12}$ seconds. This is different from the case of ion implantation which is normally done with conventional ions and where the intent is to penetrate into the material, sometimes penetrating several thousand angstroms, to produce changes in the surface properties of the material. Because of the high total energy of the cluster ion and extremely small interaction volume, the deposited energy density at the impact site is far greater than in the case of bombardment by conventional ions.

Figure 1:
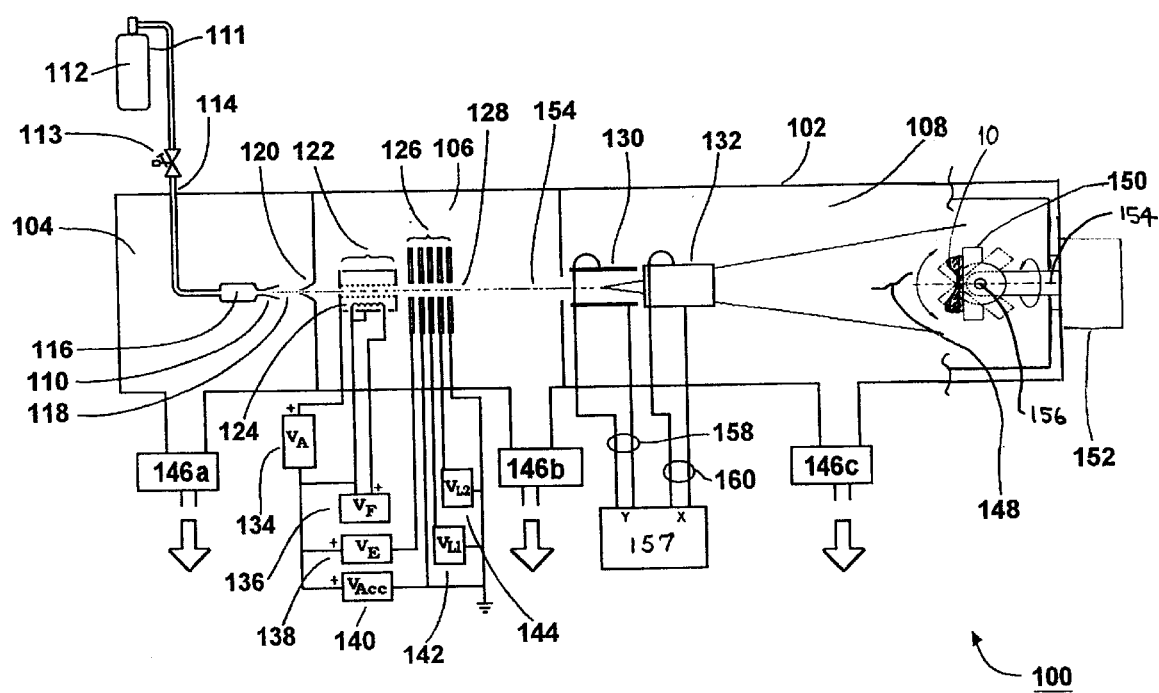
FIG. 1 is a schematic view of a gas cluster ion beam processing system of the present invention.

Reference is now made to FIG. 1 of the drawings which shows the gas cluster ion beam (GCIB) processor 100 of this invention utilized for the surface smoothing of a surgical implant such as an artificial hip joint component 10. Although not limited to the specific components described herein, the processor 100 is made up of a vacuum vessel 102 which is divided into three communicating chambers, a source chamber 104, an ionization/acceleration chamber 106, and a processing chamber 108 which includes therein a uniquely designed workpiece holder 150 capable of positioning the artificial hip joint for uniform smoothing by a gas cluster ion beam.

During the smoothing method of this invention, the three chambers are evacuated to suitable operating pressures by vacuum pumping systems 146a, 146b, and 146c, respectively. A condensable source gas 112 (for example argon, nitrogen, oxygen, or a gas mixture) stored in a cylinder 111 is admitted under pressure through gas metering valve 113 and gas feed tube 114 into stagnation chamber 116 and is ejected into the substantially lower pressure vacuum through a properly shaped nozzle 110, resulting in a supersonic gas jet 118. Cooling, which results from the expansion in the jet, causes a portion of the gas jet 118 to condense into clusters, each consisting of from several to several thousand weakly bound atoms or molecules. A gas skimmer aperture 120 partially separates the gas molecules that have not condensed into a cluster jet from the cluster jet so as to minimize pressure in the downstream regions where such higher pressures would be detrimental (e.g., ionizer 122, high voltage electrodes 126, and process chamber 108). Suitable condensable source gases 112 include, but are not necessarily limited to, argon, nitrogen, carbon dioxide, oxygen and mixtures of these gases.

After the supersonic gas jet 118 containing gas clusters has been formed, the clusters are ionized in an ionizer 122. The ionizer 122 is typically an electron impact ionizer that produces thermoelectrons from one or more incandescent filaments 124 and accelerates and directs the electrons causing them to collide with the gas clusters in the gas jet 118, where the jet passes through the ionizer 122. The electron impact ejects electrons from the clusters, causing a portion the clusters to become positively ionized. A set of suitably biased high voltage electrodes 126 extracts the cluster ions from the ionizer 122, forming a beam, then accelerates the cluster ions to a desired energy (typically from 1 keV to several tens of keV) and focuses them to form a GCIB 128 having an initial trajectory 154. Filament power supply 136 provides voltage $V_F$ to heat the ionizer filament 124. Anode power supply 134 provides voltage $V_A$ to accelerate thermoelectrons emitted from filament 124 to cause them to bombard the cluster containing gas jet 118 to produce ions. Extraction power supply 138 provides voltage $V_E$ to bias a high voltage electrode to extract ions from the ionizing region of ionizer 122 and to form a GCIB 128. Accelerator power supply 140 provides voltage $V_{ACC}$ to bias a high voltage electrode with respect to the ionizer 122 so as to result in a total GCIB acceleration energy equal to $V_{ACC}$ electron volts (eV). One or more lens power supplies (142 and 144, for example) may be provided to bias high voltage electrodes with potentials ($V_{L1}$ and $V_{L2}$ for example) to focus the GCIB 128.

A medical device such as an artificial hip joint component 10 (shown in FIG. 1 as an acetabular cup, or replaced by a femoral head) to be processed by the GCIB processor 100 is held on a workpiece holder 150, disposed in the path of the GCIB 128 (148). In order for the uniform smoothing of the hip joint component 10 to take place, the workpiece holder 150 is designed in a manner set forth below to appropriately manipulate the hip joint component 10.

Figure 2:
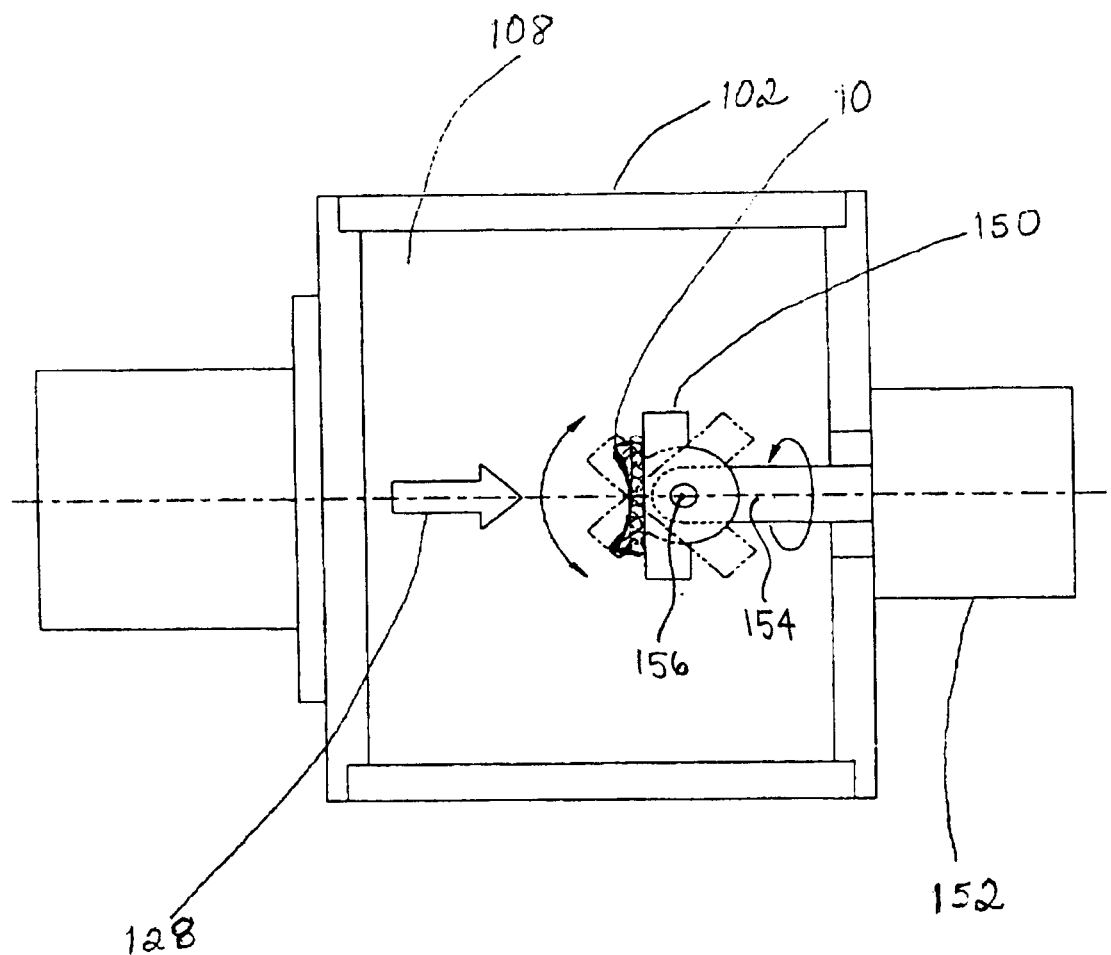
FIG. 2 is an exploded view of a portion of the gas cluster ion beam processing system showing the workpiece holder.

Referring to FIG. 2, it is desirable that the artificial hip joint surfaces that are non-planar, that is may be of a sphere-like or cup-like configuration, preferably remain oriented within a specific angle tolerance with respect to the normal beam incidence to obtain optimal smoothing of the hip joint surfaces utilizing GCIB. It has been determined that optimum smoothing occurs when the GCIB strikes the workpiece at near-normal incidence (for example within +/−15 degrees of normal), but it has also been shown that incident angles deviating up to about 45° from normal can produce effective smoothing. Additionally in the case of a cup-like joint component, it is necessary that appropriate portions of the interior surface of the cup be processed despite the fact that the rim of the cup may shadow portions of the interior surface in certain orientations. This requires a hip joint fixture or workpiece holder 150 with the ability to be fully articulated to orient all non-planar surfaces to be modified within that angle tolerance at a constant exposure level for process optimization and uniformity. More specifically, when smoothing an artificial hip joint component 10, the workpiece holder 150 is rotated and articulated by a mechanism 152 located at the end of the GCIB processor 100. The articulation/rotation mechanism 152 preferably permits 360 degrees of device rotation about longitudinal axis 154 and sufficient device articulation about an axis 156 perpendicular to axis 154 to preferably maintain the artificial hip joint surface to within +/− 15 degrees from normal beam incidence.

Under certain conditions, depending upon the size of the artificial hip joint component 10, a scanning system may be desirable to produce uniform smoothness. Although not necessary for GCIB processing, as shown in FIG. 1, two pairs of orthogonally oriented electrostatic scan plates 130 and 132 may be utilized to produce a raster or other scanning pattern over an extended processing area. When such beam scanning is performed, a scan generator 157 provides X-axis and Y-axis scanning signal voltages to the pairs of scan plates 130 and 132 through lead pairs 158 and 160 respectively. The scanning signal voltages are commonly triangular waves of different frequencies that cause the GCIB 128 to be converted into a scanned GCIB 148, which scans the entire surface of the hip joint component 10. Although electrostatic scanning of the GCIB 128 across the workpiece is illustrated, it is also possible (not shown) to achieve similar results by holding the GCIB 128 stationary and mechanically scanning the workpiece through the beam to achieve processing of large workpieces.

When beam scanning over an extended region is not desired, processing is generally confined to a region that is defined by the diameter of the beam. The diameter of the beam at the workpiece's surface can be set by selecting the voltages ($V_{L1}$ and/or $V_{L2}$) of one or more lens power supplies (142 and 144 shown for example) to provide the desired beam diameter at the workpiece.

Figure 3:
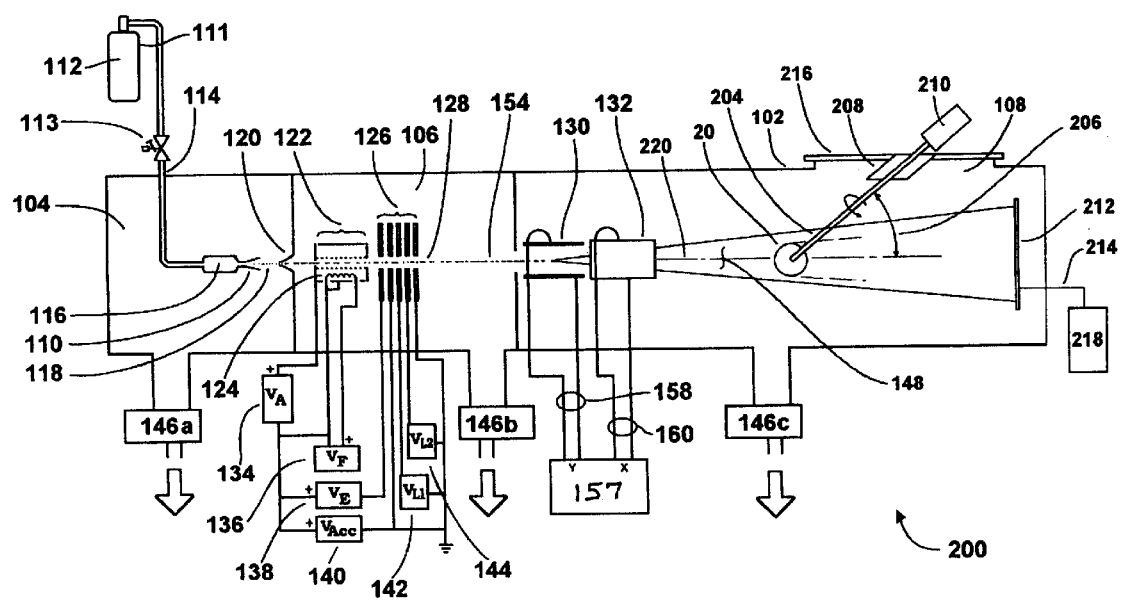
FIG. 3 is a schematic view of an alternate embodiment of a gas cluster ion beam processing system of the present invention.

FIG. 3 shows an alternate embodiment gas cluster ion beam processing system 200 of the present invention, similar to the gas cluster ion beam processing system 100 of FIG. 1, but having been configured somewhat differently for GCIB processing of sphere-like workpiece 20, for example the ball portion of a hip joint prostheses for surgical implantation. A scanned GCIB 148 is directed toward the sphere-like workpiece 20 disposed in the path of the scanned GCIB 148 in such a way that it intercepts a portion of the scanned GCIB 148. The portion of the scanned GCIB which is not intercepted by the workpiece 20 continues and strikes ion beam current collector 212, which collects electrical current due to the ions in the portion of scanned GCIB 148 that strikes the collector 212. The scanned GCIB 148 scans across a predetermined area on the surface of the current collector 212, the area including the area shadowed by the workpiece 20. The ion current collected by the charge collector 212 flows through electrical lead 214 into current integrator/processor 218, which integrates the collected current and, by taking into account the predetermined fraction of the scanned beam that is intercepted by the workpiece, calculates and displays the total dose, in ions/cm2, that would irradiate the workpiece if it were a flat surface perpendicular to the beam axis 220 and having a circular radius equal to the radius of the sphere-like workpiece 20. Workpiece 20 typically has a opening, which may be tapered, that may be used to attach it to the end of a shaft 204 and it is supported and disposed in the beam path by the shaft 204. The shaft 204 passes through rotary motion vacuum feedthrough 208 in an access plate 216 of the processing chamber 108. A conventional rotary motor 210 rotates shaft 204 and attached workpiece 20 during irradiation of the workpiece 20 by the scanned GCIB 148. The motor speed is chosen to provide a rotation period that is short compared to the processing time so that the GCIB dose is deployed circumferentially uniformly about the processed portion of the sphere-like workpiece 20. Rotary shaft 204 is disposed so that its axis of rotation is at an angle 206 to the axis 220 of scanned GCIB 148. Angle 206 is selected to determine the portion of the spherelike workpiece that receives irradiation by the GCIB 148. It is preferred that angle 206 be in the range of 20° to 50°. Because the workpiece 20 is sphere-like, the total irradiated area of the workpiece is larger than that which the scanned GCIB would irradiate if the the workpiece were a flat circular surface perpendicular to the beam axis 220 and having a circular radius equal to the radius of the sphere-like workpiece 20. The ratio of areas to the irradiated sphere-like object to that of the flat circle is given by the expression:

$$\text{Area ratio} = 2 + 2\sin(\theta), \text{ where } \theta \text{ is the angle 206} \qquad \text{Eqn. 1}$$

Accordingly, in order for the sphere-like workpiece 20 to receive a desired average dose in ions/cm2, the dose applied must be indicated by the current integrator/processor 218 to be larger than the desired dose by the factor of the Area ratio given in Eqn. 1. This assures that the average dose received by the sphere-like workpiece is equal to the desired dose, but the dose is not uniform across the surface of the sphere-like workpiece 20. If greater uniformity of dose is desired on the sphere-like workpiece or if it is desired to achieve a more limited range of GCIB incident angle on the workpiece, a more complex positioning mechanism capable of rotating the sphere about two axes can be used, like that shown in FIG. 2.

It is possible to improve the surface smoothness on artificial hip joint components 10 or 20 utilizing the present invention. A hip component 10 surface composed of a cobalt-chrome alloy had gross surface micro-roughness before GCIB treatment. The surface roughness measured an average roughness ($R_a$) of 3.86 angstroms and a root-mean-square roughness ($R_{RMS}$) of 5.28 angstroms. These irregularities highlight the surface micro-roughness problem at the cellular level where osteolysis begins. A hip joint component 10 surface composed of cobalt-chrome alloy after argon GCIB processing showed the surface micro-roughness has been reduced without any measurable physical or structural change to the integrity of the prosthesis itself. The post-GCIB surface roughness measured an $R_a$ of 2.62 angstroms and an $R_{RMS}$ of 3.34 angstroms. Effective argon gas cluster ion beam doses, using beam energies of from about 2 to about 50 keV, for smoothing cobalt-chrome alloy surfaces are typically in the range of from about $1 \times 10^{15}$ ions/cm$^2$ to about $1 \times 10^{17}$ ions/cm$^2$ and can be determined experimentally for other materials.

Figure 4:
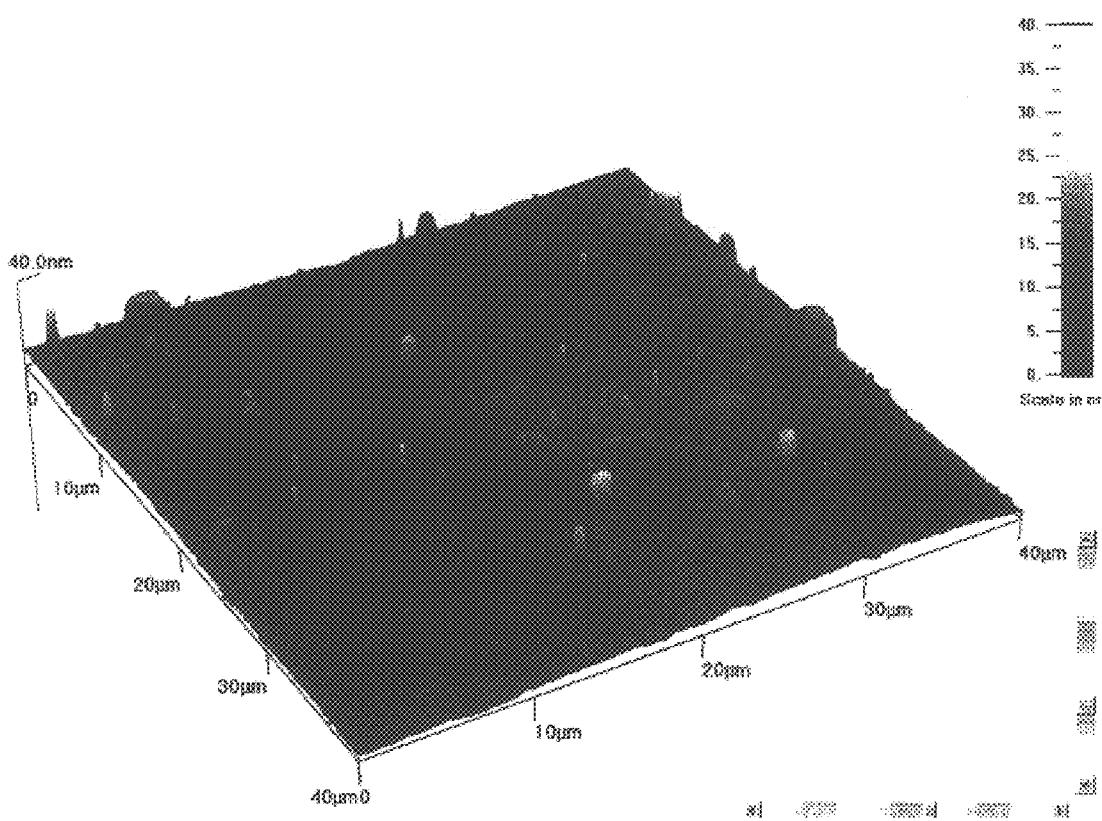
FIG. 4 is an atomic force microscope image showing the surface of a Co—Cr—Mo alloy artificial hip joint ball after conventional polishing and prior to GCIB processing.

It has been found that in some cases hip joint prosthesis components prepared and polished conventionally are considerably rougher than in the previous examples given. FIG. 4 shows an AFM image of a surface of a hip joint component 20 made from an ASTM F1537 wrought Cobalt-Chrome-Molybdenum (Co—Cr—Mo) alloy prepared and polished conventionally. The AFM-measured $R_a$ of this surface is 21.1 angstroms. It was learned that processing this surface with an argon GCIB failed to produce satisfactory reduction in the $R_a$ of the surface, even with extended processing doses. The AFM image, shown in FIG. 4, of the surface prior to GCIB processing is quite rough, with large numbers of elevated regions (asperities). The asperities are seen to fall into two size ranges when viewed on the scale of the AFM image, "small" and "larger". Experimentation revealed that the small asperities and other high spacial frequency roughness features were readily removed by GCIB processing using inert argon gas clusters. The size distribution of the asperities is clearly enough demarcated that it is believed the two sizes may arise from different phenomena. In some AFM images (not shown here) the "small" asperities have a linear streaked surface distribution that suggests that they may be some kind of residue or result of the conventional mechanical polishing process. While the "small" asperities are sometimes organized in a linear streak pattern, the "larger" ones appear randomly oriented, generally fewer in number, and somewhat platelet-like in shape.

When ASTM F1537 Co—Cr—Mo alloy is heat treated and forged, face centered cubic cobalt transforms into a hexagonal close-packed phase in the form of small platelets.

This creates a dispersion hardened material, with the platelets likely harder than the matrix. Conventional mechanical polishing can be expected to leave them exposed above the softer surface, similar to the AFM image in FIG. 4. Being harder, the platelets could be expected to be etched more slowly by the inert argon GCIB processing that successfully removes the "small" asperities and the high frequency roughness components. It was experimentally determined that by GCIB processing with a reactive gas, the "larger" platelet-like asperities could be removed, leaving in their place etched pits in the surface. It is believed that the reactive GCIB processing preferentially etches the "larger" asperities, which may be of the form of micro-grains of metal of a different phase than the matrix. This leaves a micro-pit where the "larger" asperities previously stood above the surface. Subsequent additional inert argon GCIB processing removes any sharp transitions that may otherwise remain near the pits.

Figure 5:
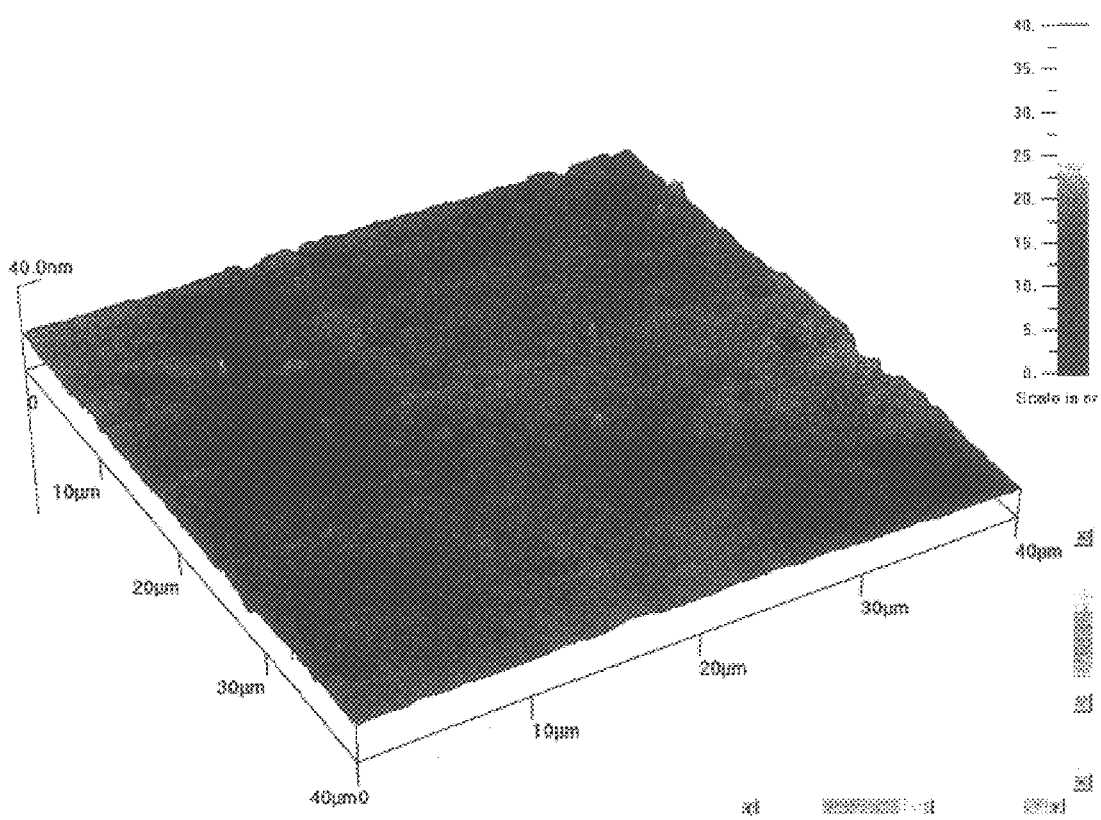
FIG. 5 is an atomic force microscope image showing the surface of the hip joint ball of FIG. 4 after GCIB processing according to a method of the invention.

FIG. 5 shows an AFM image of a surface of a hip joint component 20 composed of an ASTM F1537 wrought Cobalt-Chrome-Molybdenum (Co—Cr—Mo) alloy from the same starting sample as that of FIG. 4, but processed using a two step GCIB process according to an embodiment of the present invention. In the first step, the surface is exposed to a dose of approximately $3 \times 10^{16}$ cluster ions/cm$^2$ of clusters formed from a reactive gas, 50% argon mixed with 50% oxygen. In the second step, the surface is exposed to approximately $3 \times 10^{16}$ cluster ions/cm$^2$ of clusters formed from the inert gas, argon. The average roughness $R_a$ of this surface as measured by AFM is 15.2 angstroms, notably reduced from the 21.1 $R_a$ of the starting material previously shown in FIG. 4, with much of the residual roughness due to the presence of the micro-pits. Furthermore, the nature of the surface is transformed from a surface with elevated asperities, conducive wear and conducive to inducing wear in mating surfaces, to a largely smooth upper surface with scattered smooth micro-pits. The increased smoothness of the upper surface and the greater bearing surface is a significantly superior surface for reduced wear and particle generation in surgically implanted prostheses. Comparison of FIGS. 4 and 5 shows the dramatic surface improvement obtained by applying both reactive and inert GCIB processing to this hip joint component.

Although the invention has been described with respect to various embodiments, it should be realized this invention is also capable of a wide variety of further and other embodiments within the spirit and scope of the appended claims.

What is claimed is:

1. An apparatus for modifying a surface of a surgical implant by gas cluster ion beam processing comprising:
   a vacuum vessel;
   a gas cluster ion beam source operably associated with the vacuum vessel for producing a gas cluster ion beam;
   an accelerator for accelerating the gas cluster ion beam along a path;
   a surgical implant holder disposed substantially along a longitudinal axis within the gas cluster ion beam path, said surgical implant holder positioning the surgical implant for gas cluster ion beam processing;
   repositioning means operably connected to said surgical implant holder for rotating said surgical implant holder and the surgical implant about said longitudinal axis and articulating said surgical implant holder and the surgical implant about an axis perpendicular to said longitudinal axis.

2. The apparatus of claim 1, wherein the repositioning means articulates multiple regions of said surgical implant to intercept the gas cluster ion beam path at an angle of beam incidence that is substantially normal to the surgical implant.

3. The apparatus of claim 2, wherein the angle of beam incidence is within +/−15 degrees of normal.

4. The apparatus of claim 1 further comprising scanning means for scanning the gas cluster ion beam and the surgical implant relative to each other.

5. The apparatus of claim 1 wherein the gas cluster ion beam provides a dose of approximately $3 \times 10^{16}$ cluster ions/cm$^2$ of clusters formed from a reactive gas, 50% argon mixed with 50% oxygen.

6. The apparatus of claim 5 wherein the surgical implant comprises at least one component of an artificial hip joint.

7. The apparatus of claim 1 wherein the gas cluster ion beam provides a dose of approximately $3 \times 10^{16}$ cluster ions/cm$^2$ of clusters formed from an inert gas.

8. The apparatus of claim 7 wherein the surgical implant comprises at least one component of an artificial hip joint.

9. The apparatus of claim 1 wherein the surgical implant comprises at least one component of an artificial hip joint.

10. An apparatus for modifying a surface of a surgical implant by gas cluster ion beam processing comprising:
    a vacuum vessel;
    a gas cluster ion beam source operably associated with the vacuum vessel for producing a gas cluster ion beam;
    an accelerator for accelerating the gas cluster ion beam along a path;
    a surgical implant holder in the form of an elongated component, one end of said elongated component being removably attachable to said surgical implant;
    said elongated component being disposed at a predetermined angular relationship with respect to a longitudinal axis within said gas cluster ion beam path; and
    repositioning means operably connected to said surgical implant holder for rotating said elongated component and the surgical implant within said gas cluster ion beam path.

11. The apparatus of claim 10, wherein said elongated component positions the surgical implant to intercept the gas cluster ion beam path at an angle of beam incidence that is substantially normal to surfaces of the surgical implant.

12. The apparatus of claim 10, wherein said predetermined angular relationship with respect to a longitudinal axis within said gas cluster ion beam path is approximately 20–50 degrees.

13. The apparatus of claim 10 wherein the gas cluster ion beam provides a dose of approximately $3 \times 10^{16}$ cluster ions/cm$^2$ of clusters formed from a reactive gas, 50% argon mixed with 50% oxygen.

14. The apparatus of claim 13 wherein the surgical implant comprises at least one component of an artificial hip joint.

15. The apparatus of claim 10 wherein the gas cluster ion beam provides a dose of approximately $3 \times 10^{16}$ cluster ions/cm$^2$ of clusters formed from an inert gas.

16. The apparatus of claim 15 wherein the surgical implant comprises at least one component of an artificial hip joint.

17. The apparatus of claim 10 wherein the surgical implant comprises at least one component of an artificial hip joint.

18. A method for modifying a surface of a surgical implant by gas cluster ion beam processing to improve a surface thereof, comprising the steps of:
    forming an inert gas cluster ion beam in a vacuum chamber;

accelerating the gas cluster ion beam;

positioning a surface of the surgical implant in the vacuum chamber to receive the gas cluster ion beam for processing; and irradiating the surface with a predetermined dose of gas cluster ions having a predetermined energy.

19. The method of claim 18, further comprising the step of rotating or articulating the surgical implant to process additional regions of the surgical implant.

20. The method of claim 18, further comprising the steps of:

rotating or repositioning the surgical implant to process regions of the surgical implant; and subjecting the surgical implant to the gas cluster ion beam incident to the surgical implant substantially normal thereto.

21. The method of claim 18, wherein the surgical implant comprises a metal component.

22. The method of claim 21, wherein the metal comprises cobalt or an alloy of cobalt.

23. The method of claim 18, wherein the surgical implant comprises at least one component of an artificial hip joint.

24. A method for modifying a surface of a surgical implant by gas cluster ion beam processing to improve a surface thereof, comprising the steps of:

forming a reactive gas cluster ion beam in a vacuum chamber;

accelerating the gas cluster ion beam;

positioning a surface of the surgical implant in the vacuum chamber to receive the gas cluster ion beam for processing; and irradiating the surface with a predetermined dose of gas cluster ions having a predetermined energy.

25. The method of claim 24, further comprising the steps of:

rotating or repositioning the surgical implant to process regions of the surgical implant; and subjecting the surgical implant to the gas cluster ion beam incident to the surgical implant substantially normal thereto.

26. The method of claim 24, wherein the surgical implant comprises a metal component.

27. The method of claim 26, wherein the metal comprises cobalt or an alloy of cobalt.

28. The method of claim 24 wherein the reactive gas comprises a gas selected from the group consisting of oxygen, nitrogen, fluorine, a gaseous compound of oxygen, a gaseous compound of nitrogen, a gaseous compound of fluorine, and a mixture of an oxygen, nitrogen, or fluorine containing gas with an inert gas.

29. The method of claim 24 wherein the reactive gas comprises a mixture of about 50% oxygen with about 50% argon.

30. The method of claim 24, wherein the surgical implant comprises at least one component of an artificial hip joint.

31. A method for modifying a surface of a surgical implant by gas cluster ion beam processing to improve a surface thereof, comprising the steps of:

positioning a surface of a surgical implant in a vacuum chamber to receive one or more gas cluster ion beams for processing;

forming an accelerated reactive gas cluster ion beam with a predetermined energy in the vacuum chamber;

directing the reactive gas cluster ion beam onto a surface of the surgical implant;

irradiating the surface with a predetermined dose of the reactive gas cluster ions;

forming an accelerated inert gas cluster ion beam with a second predetermined energy in the vacuum chamber;

directing the inert gas cluster ion beam onto the surface of the surgical implant; and irradiating the surface with a predetermined dose of the inert gas cluster ions.

32. The method of claim 31, further comprising the steps of:

rotating or repositioning the surgical implant to process regions of the surgical implant; and subjecting the surgical implant to the gas cluster ion beam incident substantially normal to the surgical implant.

33. The method of claim 31, wherein the surgical implant comprises a metal component.

34. The method of claim 33, wherein the metal comprises cobalt or an alloy of cobalt.

35. The method of claim 31 wherein the reactive gas comprises a gas selected from the group consisting of oxygen, nitrogen, fluorine, a gaseous compound of oxygen, a gaseous compound of nitrogen, a gaseous compound of fluorine, and a mixture of an oxygen, nitrogen, or fluorine containing gas with an inert gas.

36. The method of claim 31 wherein the reactive gas comprises a mixture of about 50% oxygen with about 50% argon.

37. The method of claim 31, wherein the surgical implant comprises at least one component of an artificial hip joint.

* * * * *